(12) United States Patent
Stanier et al.

(10) Patent No.: US 6,479,036 B1
(45) Date of Patent: Nov. 12, 2002

(54) PARTICULATE MATERIALS FOR USE IN DENTIFRICE COMPOSITIONS

(75) Inventors: Peter W Stanier, Sandbach (GB); Charlotte R Evans, Merseyside (GB)

(73) Assignee: Crosfield Limited, Warrington (GB)

( * ) Notice: Subject to any disclaimer, the term of this patent is extended or adjusted under 35 U.S.C. 154(b) by 0 days.

(21) Appl. No.: 09/701,885

(22) PCT Filed: Jun. 1, 1989

(86) PCT No.: PCT/GB99/01718
§ 371 (c)(1),
(2), (4) Date: Dec. 5, 2000

(87) PCT Pub. No.: WO99/63958
PCT Pub. Date: Dec. 16, 1999

(30) Foreign Application Priority Data

Jun. 5, 1998 (GB) .............................................. 9812082

(51) Int. Cl.⁷ ......................... A61K 7/16; C01B 33/18; C09C 1/30; C09D 7/00; C08K 9/04
(52) U.S. Cl. ........................ 424/49; 424/489; 423/335; 423/339; 106/272; 106/288; 106/502; 51/307; 51/308; 51/309
(58) Field of Search .............................. 424/49–58, 489; 51/307, 308, 309; 106/272, 288, 502; 423/335, 339

(56) References Cited

U.S. PATENT DOCUMENTS

| | | | |
|---|---|---|---|
| 3,151,027 A | | 9/1964 | Cooley et al. ................. 167/93 |
| 3,652,420 A | * | 3/1972 | Hill ............................. 252/101 |
| 3,787,221 A | * | 1/1974 | Topcik ........................ 106/288 |
| 3,816,154 A | * | 6/1974 | Baldyga et al. .............. 106/288 |
| 3,934,000 A | * | 1/1976 | Barth ........................... 424/49 |
| 4,001,379 A | | 1/1977 | Turk et al. ................... 423/339 |
| 4,294,894 A | * | 10/1981 | Vellucci ....................... 424/49 |
| 4,632,826 A | * | 12/1986 | Ploger et al. ................. 424/52 |
| 4,837,008 A | | 6/1989 | Rudy et al. ................... 424/53 |
| 4,891,211 A | * | 1/1990 | Winston et al. ............... 424/52 |
| 4,943,429 A | * | 7/1990 | Winston et al. ............... 424/52 |
| 4,971,782 A | * | 11/1990 | Ruby et al. ................... 424/53 |
| 5,326,395 A | * | 7/1994 | Aldcroft et al. .............. 106/502 |
| 5,374,368 A | * | 12/1994 | Hauschild et al. ............ 252/95 |
| 5,424,060 A | * | 6/1995 | Hauschild et al. ............ 424/52 |
| 5,496,542 A | * | 3/1996 | Hauschild et al. ............ 424/53 |
| 5,628,985 A | * | 5/1997 | Stiller et al. .................. 424/49 |
| 5,676,933 A | * | 10/1997 | Hauschild et al. ............ 424/57 |
| 5,932,193 A | * | 8/1999 | Lopez et al. .................. 424/52 |
| 5,989,524 A | * | 11/1999 | Dromard et al. ............. 423/335 |
| 6,039,798 A | * | 3/2000 | Aldcroft et al. .............. 106/272 |
| 6,214,383 B1 | * | 4/2001 | Esch et al. ................... 424/489 |

FOREIGN PATENT DOCUMENTS

| | | |
|---|---|---|
| EP | 0193269 | 9/1986 |
| EP | 0541359 | 5/1993 |
| JP | 56068604 | 6/1981 |
| WO | WO 9708250 | 3/1997 |

\* cited by examiner

*Primary Examiner*—Shep K. Rose
(74) *Attorney, Agent, or Firm*—Pillsbury Winthrop LLP

(57) ABSTRACT

Silica particles for incorporation into a dentifrice composition, preferably as a thickening agent, have a polyether glycol such as polyethylene glycol applied thereto in order to enhance dentifrice cohesion

4 Claims, No Drawings

PARTICULATE MATERIALS FOR USE IN DENTIFRICE COMPOSITIONS

This invention relates to particulate materials, such as synthetic amorphous silicas, especially precipitated silicas, for use in dentifrice compositions and especially for use as thickening agents in such compositions. The invention is also concerned with dentifrice compositions containing such particulate materials.

Dentifrice compositions contain a number of specific components, for example particulate materials such as amorphous silicas, fluoride sources, viscosity regulating agents, preservatives, humectants, surfactants, anti-plaque agents, anti-tartar agents, anti-hypersensitivity agents, colouring agents, water, flavour and other optional ingredients, the particulate materials being employed for their thickening and/or abrasive properties.

Typically the humectant system is based on an edible polyhydric alcohol, such as glycerine, sorbitol, polypropylene glycol, polyethylene glycol (PEG) or any suitable mixture thereof, to prevent the toothpaste from drying out. Optionally, polyethylene glycol can be employed to regulate the viscosity and cohesiveness of the formulation see for example U.S. Pat. No. 3,689,637. Compared with glycerine or sorbitol for example, PEG is a relatively expensive component of a dentifrice formulation.

According to one aspect of the present invention there is provided a particulate material for use in a dentifrice composition, the particulate material comprising silica particles to which a polyether glycol has been applied.

Preferably the silica particles have a relatively high structure so that they would already act as a thickening agent when incorporated in a dentifrice composition, if the polyether glycol had not been applied. Suprisingly, the application of the polyether glycol to the silica gives a further enhancement of thickening over a naked silica with the same structure, in a dentifrice formulation.

Some dentifrice formulations already contain a polyether glycol. By using silica particles to which a polyether glycol such as polyethylene glycol has already been applied, at least part of the polyether glycol employed in the dentifrice composition may be introduced through the agency of the particulate material. Surprisingly by intimately associating the polyether glycol with the particulate material, the amount required in the dentifrice composition can be reduced significantly to achieve a predetermined cohesion. In addition, by applying a suitable polyether glycol to the particulate material, the production of the particulate material by wet processing may be facilitated since the viscosity regulating agent may be beneficial to filtration efficiency.

According to a second aspect of the present invention there is provided a dentifrice composition, which includes water, humectant and a dispersed particulate material (preferably acting as a thickening agent), characterised in that the particulate material comprises silica particles to which a polyether glycol has been applied prior to incorporation of the particles in the composition.

Advantageously, it has been found that substantially less polyether glycol is required to provide a specific dentifrice cohesion, when the polyether glycol present in the dentifrice composition is carried by the silica particles rather than being present as a separate component within the dentifrice. In high water transparent toothpaste formulations, where good transparency can only be achieved in the absence of PEG, this is particularly advantageous. The removal of PEG from the formulation to achieve good transparency reduces the cohesion of dentifrice. The dentifrice cohesion can be recovered by incorporation of a silica of the invention in which the polyether glycol is carried by the silica.

Furthermore, a greater dentifrice cohesion can be achieved if the polyether glycol is carried by the silica, than if the same amount of polyether glycol is added as a separate component to the formulation. Also, the polyether treated silica particles provide a higher cohesion toothpaste than the same silica particles without polyether treatment, when incorporated at the same loading by weight.

The polyether glycol is typically constituted by polyethylene glycol and/or polypropylene glycol having an average molecular weight (i.e., number-average molecular weight in the range of 200 to 20,000. A presently preferred polyethylene glycol (PEG) is one having an average molecular weight in the range 4,000 to 12, 000, preferably 5,000 to 10,000 and more preferably about 5,000 to 7,000, e.g. about 6,000.

Usually the dentifrice composition will be in the form of a toothpaste, gel, cream or liquid, of the opaque, translucent or transparent variety. The exact physical properties of the dentifrice composition may be controlled for example by suitable adjustment of the water, humectant and dispersed particulate material (thickening silica).

The humectant component of the composition may comprise a polyol such as glycerol, sorbitol syrup, polypropylene glycol, lactitol, xylitol or hydrogenated corn syrup. The total amount of humectant may for example be in the range of 10 to 85% by weight of the composition.

The water content of the dentifrice composition typically ranges from 1 to about 90% by weight, preferably from about 10 to about 60% by weight, more preferably from about 15 to about 50% by weight. In the case of transparent pastes, a preferred range is from about 1 to about 35% by weight.

In preferred embodiments of the invention, the polyether glycol-carrying silica particles particulate material are present in the composition in a total amount of from about 0.1 to about 50% by weight; preferably from about 0.5 to 15% and most preferably from about 1 to 10% by weight.

The dentifrice composition of the invention may additionally comprise one or more additional components, such as those described below.

The composition of the invention may include one or more surfactants, preferably selected from anionic, non-ionic, amphoteric and zwitterionic surfactants, and mixtures thereof, all being suitable for dental and/or oral use. The amount of surfactant present in the composition of the invention is typically from about 0.1 to about 3% by weight (based upon 100% activity).

Suitable anionic surfactants may include soaps, alkyl sulphates, alkyl ether sulphates, alkaryl sulphonates, alkanoyl isethionates, alkanoyl taurates, alkyl succinates, alkyl sulphosuccinates, N-alkoyl sarcosinates, alkyl phosphates, alkyl ether phosphates, alkyl ether carboxylates and alpha-olefin suiphonates, especially their sodium, magnesium, ammonium and mono-, di- and triethanolamine salts. The alkyl and acyl groups generally contain from 8 to 18 carbon atoms and may be saturated. The alkyl ether sulphates, alkyl ether phosphates and alkyl ether carboxylates may contain from one to 10 ethylene oxide or propylene oxide units per molecule, and preferably 2 to 3 ethylene oxide units per molecule. Examples of preferred anionic surfactants include sodium lauryl sulphate, sodium dodecylbenzene sulphonate, sodium lauroyl sarcosinate and sodium coconut monoglyceride sulphonate.

Non-ionic surfactants which may be suitable for use in the composition of the invention include sorbitan and polyglycerol esters of fatty acids, as well as ethylene oxide/propylene oxide block copolymers.

Suitable amphoteric surfactants include betaines such as cocamidopropyl betaine and sulphobetaines.

The dentifrice composition of the invention may also incorporate suitable well known polymer suspending or thickening agents such as polyacrylic acid, copolymers and cross-linked polymers of acrylic acid, copolymers of acrylic acid with a hydrophobic monomer, copolymers of carboxylic acid-containing monomers and acrylic esters, cross-linked copolymers of acrylic acid and acrylate esters, esters of ethylene glycol or esters of polyethylene glycol (e.g. fatty acid esters thereof, heteropolysaccharide gums such as xanthan and guar gums, and cellulose derivatives such as sodium carboxymethyl cellulose. Particularly suitable thickening agents are as mixtures of two or more of the above materials) may be present in the composition in a total amount of from about 0.1 to about 5% by weight.

One or more other components that are conventionally found in an oral composition may be present in the dentifrice composition and include the following; flavouring substances such as peppermint, spearmint; artificial sweeteners; perfume or breath freshening substances; peariescing agents; peroxy compounds such as hydrogen peroxide or peracetic acid; opacifiers; pigments and colourings; preservatives; moisturising agents; fluoride-containing compounds; anti-caries and anti-plaque agents; anti-tartar agents; anti-hypersensitivity agents; therapeutic agents such as zinc citrate, Triclosan (ex Ciba Geigy); proteins; enzymes; salts; baking soda and pH adjusting agents. Furthermore, the dentifrice compositions usually comprise additional abrasive cleaning agents in an amount from about 1 to 60% by weight. These include abrasive silicas, chalks, hydrated aluminas, calcium phosphate, calcium pyrophosphate, hydroxyapatites, insoluble metaphosphates etc.

Dentifrice compositions in accordance with the invention may be made by conventional methods of preparing such compositions. Pastes and creams may be prepared by conventional techniques, for example using high shear mixing systems under vacuum.

The most suitable silica particles for application of the polyether glycol are those which would already give a thickening effect to a dentifrice composition in the absence of a polyether glycol i.e. medium, high and very high structured silicas. These can be further quantified as silicas with oil absorption above about 125, preferably 200 cm$^3$/10 g; mercury intrusion void volume above about 2.0, preferably 3.0, most preferably 4.0 cm$^3$/ g; weight mean particle size up to about 30 microns (preferably up to about 20 microns) and a moisture loss at 105° C. of less than about 25, preferably 15% by weight.

According to a further aspect of the invention there is provided a process for the production of a particulate silica material in which the silica is prepared by contacting an alkali metal silicate solution with an acid to produce silica which is then comminuted to a desired particle size, characterised in that a polyether glycol is combined with the silica so formed before or after comminution to the desired particle size.

The silica particles thus obtained may then be incorporated in dentifrice compositions of various types, e.g. opaque, translucent or transparent dentifrices, in order to control its cohesion.

Measurement of Parameters and Definitions Oil Absorption

The oil absorption is determined by the ASTM spatula rub-out method (American Society of Test Material Standards D, 281). The test is based on the principle of mixing linseed oil with the silica by rubbing with a spatula on a smooth surface until a stiff putty-like paste is formed which will not break or separate when it is cut with a spatula. The oil absorption is then calculated from the volume of oil (V cm$^3$) used to achieve this condition and the weight W in grams of particulate matter by means of the equation:

Oil absorption=(V×100)/W, i.e. expressed in terms of cm$^3$ oil/100 g particulate matter.

Weight Mean Particle Size

The weight mean particle size of the silica is determined using a Malvern Mastersizer model X, with a 45 mm lens and MS 15 sample presentation unit. This instrument, made by Malvern Instruments, Malvern, Worcestershire uses the principle of Fraunhoffer diffraction, utilising a low power He/Ne laser. Before measurement the sample is dispersed ultrasonically in water for 7 minutes to form an aqueous suspension. The Malvern Mastersizer measures the weight particle size distribution of the silica. The weight mean particle size ($d_{50}$) or 50 percentile is easily obtained from the data generated by the instrument.

Electrolyte Levels

Sulphate is determined gravimetrically by hot water extraction of the silica, followed by precipitation as barium sulphate. Chloride is determined by hot water extraction of the silica, followed by titration with standard silver nitrate solution using potassium chromate as indicator (Mohr's method).

Moisture Loss at 105° C.

Moisture loss is determined by the loss in weight of a silica when dried to constant weight in an electric oven at 105° C.

Ignition Loss at 1000° C.

Ignition loss is determined by the loss in weight of a silica when ignited in a furnace at 1000° C. to constant weight.

pH

This measurement is carried out on a 5% w/w suspension of the silica in boiled demineralised water ($CO_2$ free).

Mercury Intrusion Void Volume

Mercury intrusion void volumes are determined (in cc/g) by standard mercury intrusion procedures using a Micromeritics Autopore 9220 mercury porosimeter. Prior to measurement the sample is outgassed at room temperature to a pressure of 50 microns of mercury. Mercury is forced into the voids as a function of pressure and the volume of mercury intruded per gramme of sample is calculated at each pressure setting. The mercury intrusion volume recorded is that occurring at pressures from vacuum to 60,000 psi. and represents the cumulative volume of mercury intruded.

Toothpaste Refractive Index (RI)

This measurement is carried out using an Abbe 60 refractometer, supplied by Bellingham & Stanley Ltd, Tunbridge Wells, Kent, England. Measurements are made at 25° C. in accordance with the operating instructions. 1–2 g of the toothpaste sample under examination is placed on the lower prism face of the refractometer and the upper prism face is lowered to leave a thin film of toothpaste between the faces of the prism. Adjustments are made to ensure the sharpest contrast between the light and dark portions of the field. The position of the light and dark interface is adjusted until it intersects the crosswires. The refractive index of the toothpaste is noted to four decimal places.

Toothpaste Cohesion

The cohesion of a toothpaste is a good measure of the "stand-up" properties of the ribbon when it has been extruded from a toothpaste tube onto a toothbrush. Higher cohesion values indicate firmer toothpaste ribbons, whereas low cohesion numbers are obtained from low viscosity, poorly structured toothpastes, which quickly sag into the bristles of the brush. It is generally required that a dentifrice has a cohesion within the range of 150–430g to provide a good quality, extrudable ribbon, which does not sag and is not too firm.

The basic principle of the test is to measure the weight in grammes required to pull two parallel plates apart, which have a specific layer of toothpaste sandwiched between them. The purpose built equipment consists of:

1) A spring balance in which the spring can be extended from 0–430 g in 100 mm of length.
The spring has a calibration scale of zero to 430 g in 10 g intervals and can be adjusted to zero at the start of the test.
2) A motor driven ratchet, which is attached to the bottom plate and can be used to apply a constant, uniform, smooth vertical pull on the bottom plate of 5 cm per minute.
3) An upper polished chrome circular plate of 64 mm diameter, which has a hook on the upperside that can be attached to the spring balance. The polished plate has three small identical spacer pieces of polished chrome on the underside of the plate, as an integral part of the plate. These protrude to a depth of 4 mm, which determines the toothpaste film thickness when the equipment is assembled to carry out the test.
4) A lower polished chrome circular plate of 76 mm diameter, which is attached underneath to a motor driven ratchet. Two short pegs are located on the top of the plate so that the top plate can be positioned on the bottom plate concentrically from the centres.
5) A metal framework which allows the top plate to be situated concentrically above the bottom plate and the bottom plate to be adjusted so that the plate is approximately horizontal (achieved through the use of levelling feet on the base of the equipment).

15–20 g of toothpaste is evenly distributed onto the underside of the upper plate and the plate is carefully positioned onto the top of the bottom plate, using the two short pegs to locate the edge of the top plate. The top plate is firmly pressed down onto the bottom plate, until all three spacers have made contact with the bottom plate. Excess toothpaste, which has been squeezed out from between the two plates is then removed with a spatula, such that no toothpaste extends beyond the diameter of the top plate. The upper plate is then connected to the spring balance and the scale set to zero grammes. The equipment is then switched on to allow the motor driven ratchet to lower the bottom plate. The spring is gradually extended and the highest observed weight is noted, as the two parallel plates sandwiched with toothpaste are eventually pulled apart. This is the toothpaste cohesion recorded in grammes.

Clarity

The principle of this test is to determine the point at which different size letters and numbers on a test card can be read through a toothpaste of specific thickness.

The test is conducted using the RIT ALPHANUMERIC RESOLUTION TEST OBJECT, RT-4-74 produced by the Graphic Arts Research Centre, Rochester Institute of Technology, 1, Lomb Memorial Drive, Rochester, N.Y. 14623. This has a scale of minus 12 to plus 13 of very large (10 by 10 mm), through to very small (0.4 by 0.4 mm), numbers and letters on 26 different lines. Positive numbers indicate transparent toothpastes, with higher positive numbers giving better clarity and +13 giving the best clarity.

A cuvette with a 1 cm path length is filled with the toothpaste to be tested. The cuvette is placed upon the chart and the clarity value determined by noting the smallest line on the chart that can be clearly read through the cuvette.

Specific Description of the Invention

The invention will now be further described in the following Examples. The first Example illustrates one method of preparing a polyether glycol treated silica; however, the invention is not limited to this particular preparation method.

EXAMPLE 1

A heated stirred reaction vessel was used for the silicate/acid reaction. Mixing is an important feature in the reaction of silicate and sulphuric acid. Consequently fixed specifications, as listed in Chemineer Inc. Chem Eng. 26 April 1976 pages 102–110, have been used to design the baffled, heated stirred reaction vessel. Whilst the turbine design is optional to the mixing geometry, a 6-bladed 300 pitched bladed unit has been chosen for the experiments in order to ensure maximum mixing effectiveness with minimum shear.

The solutions used in the process were as follows:
a) Sodium silicate solution with an $SiO_2:Na_2O$ weight ratio of 3.29 and an $SiO2$ content of 16.6% w/w
b) A sulphuric acid solution of specific gravity 1.12 (17.4% w/w solution).

The following procedure was adopted for the preparation of a precipitated silica and its subsequent treatment with a polyether glycol.

142.5 litres of water was placed in a 300 litre capacity vessel with 1.15 litres of sodium silicate solution. This mixture was stirred and heated to 94° C. 114 litres of sodium silicate and 42 litres of sulphuric acid were then simultaneously added over 20 minutes at 94° C. The flow rates of the silicate and acid solutions were uniform throughout the addition period to ensure that a constant pH, in the range from 10 to 11, was maintained in the vessel. The slurry was then adjusted with sulphuric acid over a ten minute period to the final end of batch pH 4.5.

At this point the final slurry was split. One half of the final slurry was filtered and washed with water to remove excess electrolyte. Typically, for a toothpaste application, the residual electrolyte would be less than 2% on a dry weight basis. The resulting silica is referred to below as the standard silica. To the second half of the final slurry, 393 g of polyethylene glycol with 6000 molecular weight (PEG 6000) was added and mixing was effected for a period of 30 minutes at temperature 60° C. and a pH of 4.5. The treated slurry was then filtered and washed in the same manner as described above. The silica derived from the second part is referred to as a silica of the invention. After washing, each filter cake was flash dried to remove the water rapidly from the silica so that the structure was maintained, and comminuted. The silica of the invention was comminuted to two different particle sizes, identified as silica of the invention (1) and (11).

The typical physical properties of the precipitated silicas produced are listed in Table 1.

An alternative route for application of the polyether glycol to the silica particles is to take the silica particles herein defined, re-slurry them in water and add the polyether to it until fully dispersed in solution. The treated particles are then filtered, dried and (optionally) comminuted to the required particle size.

A further alternative treatment method is to spray a solution of the polyether glycol onto the silica particles as a coating, for example in a fluidised bed, followed by a drying and (optionally) a comminution step. All of these methods are effective in applying the polyether glycol to the particulate material, although application during the silica manufacturing process is preferred on cost and processing grounds.

TABLE 1

| TEST | Std Silica | Silica of the Invention (I) | Silica of the Invention (II) |
|---|---|---|---|
| Oil Absorption) (cm$^3$/100 g) | 233 | 225 | 269 |
| pH | 6.4 | 5.9 | 6.1 |

The amorphous silicas described above were added at the same percentage weight loading (11%) to opaque dentifrice formulation A (Examples 2,3 & 4—see Table 3). Whilst all three toothpastes had commercially suitable properties for stability and usage, incorporation of the silicas (I) & (II) of the invention into the toothpaste formulation showed improved structure as determined by the cohesion measurement, irrespective of the particle size.

Replacement of the free polyethylene glycol 1500 by sorbitol in toothpaste formulation A (i.e. formulation B), utilising the standard silica of example 1 (Example 5) produces a lower structured toothpaste with a corresponding drop in cohesion. However, Example 6, using the silica of the invention (1) in the same formulation shows that the toothpaste has similar structural properties to Example 2.

Example 7 illustrates the effect of only having a small quantity of PEG1500 in toothpaste formulation A (i.e. formulation C), the quantity being similar to the treated polyethylene glycol found on the silica of the invention. Comparison of Example 7 with Example 5 shows that although the addition of a small amount of PEG1500 improves the structural properties of the toothpaste, the increase in structure is not as great as when the standard silica is pre-treated with polyethylene glycol (Example 6).

TALE 2

| INGREDIENT | Formulation A Loading (% w/w) | Formulation B Loading (% w/w) | Formulation C Loading (% w/w) |
|---|---|---|---|
| Water | 27.28 | 27.28 | 27.28 |
| Sorbitol | 44.0 | 49.0 | 48.88 |
| Standard Silica or silica of the invention (I or II) | 11.0 | 11.0 | 11.0 |
| Sorbisol AC35* | 8.0 | 8.0 | 8.0 |
| ("free") PEG 1500 | 5.0 | 0 | 0.12 |
| SLS | 1.5 | 1.5 | 1.5 |
| Flavour | 1.0 | 1.0 | 1.0 |
| NaF | 0.22 | 0.22 | 0.22 |
| TiO$_2$ | 1.0 | 1.0 | 1.0 |
| Saccharin | 0.2 | 0.2 | 0.2 |
| Sodium Benzoate | 0.1 | 0.1 | 0.1 |
| SCMC | 0.7 | 0.7 | 0.7 |

(*- abrasive silica produced by Crosfield Ltd, Warrington, England)

TABLE 1-continued

| TEST | Std Silica | Silica of the Invention (I) | Silica of the Invention (II) |
|---|---|---|---|
| Weight Mean Particle Size (microns) (Malvern) | 14.9 | 11.0 | 13.2 |
| Moisture loss at 105° C. | 4.5 | 5.1 | 2.2 |
| Ignition Loss at 1000° C. | 8.3 | 9.5 | 6.8 |
| SO$_4^{2-}$(%) | 0.39 | 0.43 | 0.55 |
| PEG 6000 (% w/w) | 0 | 1.27 | 1.36 |

DENTIFRICE EXAMPLES 2, 3, 4, 5, 6 & 7 (TABLE 3)

Table 2 gives the compositions of a number of toothpaste formulations incorporating the high structure silica produced by the process described in example 1 above, the silica being either the standard silica (without PEG 6000) or the silica of the invention (1) or (11) i.e. with PEG 6000 applied to the silica.

TABLE 3

| | Silica | Formulation | Cohesion (g) |
|---|---|---|---|
| Example 2 | Standard Silica | A | 340 |
| Example 3 | Silica of the Invention (I) | A | 390 |
| Example 4 | Silica of the Invention (II) | A | 430 |
| Example 5 | Standard Silica | B | 145 |
| Example 6 | Silica of the Invention (I) | B | 330 |
| Example 7 | Standard Silica | C | 190 |

Note:
Examples 2, 5 and 7 are comparative Examples.

EXAMPLES 8, 9, 10, 11, 12 AND 13 (TABLE 5)

The silica of the invention was also formulated into high water transparent dentifrice formulations (D, E and F—see Table 4) and compared against the standard silica. The results are shown in Table 5:

TABLE 4

| INGREDIENT | Formulation D LOADING (% w/w) | Formulation E LOADING (% w/w) | Formulation F LOADING (% w/w) |
|---|---|---|---|
| Sorbitol | 60.5 | 63.75 | 63.65 |
| Water | 16.3 | 16.01 | 16.02 |
| Standard Silica or Silica of the Invention (1) | 10.0 | 10.0 | 10.0 |
| Abrasive silica (*) | 6.0 | 6.0 | 6.0 |
| ("free") PEG 1500 | 3.0 | 0 | 0.12 |
| SLS | 1.5 | 1.5 | 1.5 |
| Flavour | 1.0 | 1.0 | 1.0 |
| SMFP | 0.8 | 0.8 | 0.8 |
| SCMC | 0.7 | 0.7 | 0.7 |
| Saccharin | 0.2 | 0.2 | 0.2 |
| Blue Dye | 0.001 | 0.001 | 0.001 |

(* Abrasive silica produced according to PCT Patent Application No. WO 94/10087)

TABLE 5

| | Silica | Formulation | Cohesion (g) | Apparant Refractive Index | Clarity |
|---|---|---|---|---|---|
| Example 8 | Standard Silica | D | 365 | 1.438 | −6 |
| Example 9 | Standard Silica | E | 220 | 1.438 | 7 |
| Example 10 | Standard Silica | F | 300 | 1.436 | −6 |
| Example 11 | Silica of the Invention (1) | D | >430 | 1.438 | −10 |
| Example 12 | Silica of the Invention (1) | E | >430 | 1.439 | 8 |

Note:
Examples 8, 9 and 10 are comparative Examples.

Inclusion of a second humectant (PEG 1500) in a high water gel toothpaste (formulation D) does not produce a visually clear paste (Examples 8 & 11). Even a small addition (0.12% PEG 1500—formulation F) has an adverse effect upon the final toothpaste clarity (Example 10). Removal of the second humectant (PEG 1500—formulation E) results in a visually clear paste, but the structure of the final paste reduces dramatically using the standard silica (Example 9). Replacement of the standard silica with the silica of the invention (1) in Example 12 shows that the structure of the toothpaste is maintained without an adverse effect upon the final paste clarity.

What is claimed is:

1. A process for the production of a particulate silica material useful in a dentifrice composition, comprising (a) preparing a thickening silica by contacting an alkali metal silicate solution with an acid to produce said thickening silica, (b) comminuting the thickening silica to a weight mean particle size up to 30 microns, (c) combining an aqueous solution of a polyether glycol selected from the group consisting of polyethylene glycols and polypropylene glycols and having a molecular weight in the range of 200 to 20,000 with the said thickening silica before or after comminution to the said particle size, and (d) drying the silica.

2. A process as claimed in claim 1 wherein the silica is a precipitated silica.

3. A process according to claim 1, wherein the polyether glycol is polyethylene glycol having an average molecular weight in the range of 5,000 to 10,000.

4. A process according to claim 1, wherein the silica has an oil absorption above 125 $cm^3$/100 g, a mercury intrusion volume above 2.0 $cm^3$/g and a moisture loss at 105° C. of less than 25% by weight.

* * * * *

UNITED STATES PATENT AND TRADEMARK OFFICE
CERTIFICATE OF CORRECTION

PATENT NO.   : 6,479,036 B1
DATED        : November 12, 2002
INVENTOR(S)  : Stanier et al.

It is certified that error appears in the above-identified patent and that said Letters Patent is hereby corrected as shown below:

<u>Title page,</u>
Item [22], correct the filing date of the PCT application to read:

-- [22]  PCT Filed: Jun. 1, 1999 --.

Signed and Sealed this

Eighth Day of April, 2003

JAMES E. ROGAN
*Director of the United States Patent and Trademark Office*